United States Patent [19]

Uehara et al.

[11] Patent Number: 5,554,370
[45] Date of Patent: Sep. 10, 1996

[54] METHOD FOR THE TREATMENT OF INFLAMMATORY BOWEL DISEASES

[75] Inventors: Yasuo Uehara, Iruma; Michihito Ise, Kawagoe, both of Japan

[73] Assignee: Kureha Kagaku Kogyo Kabushiki Kaisha, Japan

[21] Appl. No.: 450,469

[22] Filed: May 25, 1995

[30] Foreign Application Priority Data

May 27, 1994 [JP] Japan ................................ 6-138071

[51] Int. Cl.⁶ .................................................. A01N 59/00
[52] U.S. Cl. .................................................. 424/125
[58] Field of Search ............................................. 424/125

[56] References Cited

U.S. PATENT DOCUMENTS

| | | | |
|---|---|---|---|
| Re. 29,101 | 1/1977 | Amagi et al. | 423/449 |
| 3,917,806 | 11/1975 | Amagi et al. | 252/421 |
| 4,420,443 | 12/1983 | Kaji et al. | 264/15 |
| 4,681,764 | 7/1987 | Endo et al. | 424/125 |
| 4,761,284 | 8/1988 | Nishimura | 424/125 |

FOREIGN PATENT DOCUMENTS 61-1386 of 1986 Japan.

*Primary Examiner*—James J. Seidleck
*Assistant Examiner*—Terressa Mosley
*Attorney, Agent, or Firm*—Nixon & Vanderhye

[57] ABSTRACT

The disclosure describes a method of treating a patient suffering from inflammatory bowel diseases, comprising orally administering to said patient an effective amount of a pharmaceutical composition in dosage unit form comprising a spherical activated carbon having a particle size of 0.05 to 2 mm.

12 Claims, No Drawings

METHOD FOR THE TREATMENT OF INFLAMMATORY BOWEL DISEASES

BACKGROUND OF THE INVENTION

The present invention relates to a method for the treatment of inflammatory bowel diseases, and more in detail, to a method for the treatment of inflammatory bowel diseases, comprising administering to a patient a pharmaceutical composition for inflammatory bowel diseases, which comprises a spherical activated carbon as active ingredient.

Inflammatory bowel disease (IBD) is a general term for the intestinal troubles with an inflammation. The representative cases of inflammatory bowel diseases are ulcerative colitis and Crohn's disease of unknown etiology. No effective therapeutic method is available for either of these diseases.

Ulcerative colitis is an unaccountable disease of diffuse nonspecific inflammation of the colon which attacks the mucous membrane and often forms an erosion or ulcer. The lesion is chiefly submucosal. The clinical symptoms of this disease are viscous-hemafecia, celialgia, hemafecia, watery stool, fervescence, loss of appetite, nausea and vomiting. Also, ulcerative colitis may be attended by such troubles as arthritis, stricture of the large intestine and copious bleeding, but their incidence is not high. Salazosulfapyridine (Salazopyrin®), adrenocortical steroids, immuno-suppressants and the like are used as therapeutic agents for ulcerative colitis, but these medicines are unsatisfactory in these therapeutic effect therefor.

Crohn's disease is an idiopathic chronic enteritis of unknown etiology. This disease occurs most frequently in human beings of both sexes in their twenties and becomes chronic. It is a granulomatous lesion with fibrosis or ulceration and may be attacked with in the whole alimentary tract from mouth to anus. The clinical symptoms of Crohn's disease are celialgia, general malaise, diarrhea, melena and occult bleeding positive, fervescence, loss of body weight, anemia, ileus, abdominal tumor and peritonitis.

Crohn's disease tends to cause trophic disturbance and various other serious digestive and extra intestinal complications such as intestinal stenosis, abdominal abscess, copious bleeding, intestinal perforation, etc., which usually necessitate an enteric operation. Relapse of the disease after the operation occurs at a high percentage. Therefore, no surgical treatment is conducted unless the irreversible imperforation is combined therewith or curative excision is required. For this reason, the treatment by medication is being tried. For medication, there are used salazosulfapyridine (Salazopyrin®), metronidazole (Flagyl®), adrenocortical steroids, immuno-suppressants and the like. These medicines, however, are unsatisfactory in their therapeutic effect for Crohn's disease.

Treatments based on nutrition therapies are now applied for Crohn's disease, and the methods are employed that can heighten the "quality of life" (QOL) of the patient, which includes rehabilitation, and can facilitate remission of the disease.

Salazosulfapyridine used as the medicine for inflammatory bowel diseases is liable to cause adverse reactions or side effects such as abdominal fullness, headache, exanthema, hepatic disorder, leukopenia, agranulocytosis, male sterility, etc. It is also unclear whether this salazosulfapyridine has sufficient relapse suppressive effect in the patient after resection of the affected part of the intestine or in the patient in remission. As for metronidazole, although its potency is admitted in the data on antiphlogistic effect in the reports of control tests, its utility for the clinical improvement is unclear.

Adrenocortical steroids, although their short-time effect has been admitted, are unable to improve long-time prognosis, and it is considered that they should be used for the acute cases only, in view of their side effects such as induced infectious diseases, secondary adrenocortical insufficiency, peptic ulcer, diabetes, mental disorder, steroidal renal trouble, etc. Also, when adrenocortical steroids are administered to the patient having a fistula or abscess, it is liable to cause worsening of infection or delay cure of the lesion to complicate the disease. Immunosuppressants are used for the cases where the side effects of adrenocortical steroids were produced, but the effect of the immuno-suppressants is skeptical and also they have a possibility of inviting a horrific side effect such as carcinogenesis.

As viewed above, no reliable therapy is yet available for the inflammatory bowel diseases, and the development of an effective therapeutic agent for these diseases has been desired. Especially in the case of Crohn's disease, the complicated cases of anal lesion such as anal fistula and hemorrhoids, which develop symptoms at an early stage and may impair QOL in the long process, have a high percentage of occurrence (about 90%) and defy the internal therapies, so that the frequent surgical treatments are necessitated, which gives a great deal of discomfort to the patient. Also, when the affected part of the intestine is resected and a stoma is provided, there may take place such troubles as contact dermatitis, itching, redness, ulceration and other types of inflammation on the skin around preternatural anus, which are complicated diseases, to give great discomfort to the patient.

Under these circumstances, development of an effective therapeutic agent for the inflammatory bowel diseases has been demanded.

As the result of the present inventors' pursued researches on the effective therapeutic agents for inflammatory bowel diseases, especially Crohn's diseases, which are different from the conventionally used medicines, it has been found that a prominent therapeutic effect for inflammatory bowel diseases is produced by oral administration of a spherical activated carbon. Spherical activated carbons have been generally used as an oral therapeutic agent for chronic renal failure, but no report has ever been made on use of such spherical activated carbon as a therapeutic agent for the inflammatory bowel diseases, especially Crohn's disease. In view of this circumstance, the above finding by the present inventors is deemed an unexpected fact based on a novel conception. The present invention has been attained on the basis of the above finding.

SUMMARY OF THE INVENTION

An object of the present invention is to provide a pharmaceutical composition and a method for treating inflammatory bowel diseases, which show an excellent therapeutic effect, without causing any specific side effects, for the inflammatory bowel diseases which had hitherto no effective cure.

Another object of the present invention is to provide a pharmaceutical composition and a method for treating Crohn's diseases, which show an excellent therapeutic effect, without causing constipation or other adverse reactions.

Still another object of the present invention is to provide a pharmaceutical composition and a method for treating complicated diseases of the inflammatory bowel diseases with hemorrhoidal diseases and/or stoma-peripheral inflammation diseases.

To attain the above aims, in a first aspect of the invention, there is provided a method of treating a patient suffering from an inflammatory bowel disease, especially Crohn's disease, comprising orally administering to the patient an effective amount of a pharmaceutical composition in dosage unit form comprising a spherical activated carbon having a particle size of 0.05 to 2 mm.

In a second aspect of the invention, there is provided a method of treating a patient suffering from an inflammatory bowel disease, especially Crohn's disease, comprising orally administering to the patient an effective amount of a pharmaceutical composition in dosage unit form comprising a spherical activated carbon having a particle size of 0.05 to 2 mm and produced by heat-treating a porous and spherical carbonaceous substance obtainable from a petroleum-based heavy hydrocarbon (petroleum pitch) in an oxidative atmosphere and further heat-treating the thus obtained substance in an atmosphere inert to carbon.

In a third aspect of the invention, there is provided a method of treating a patient suffering from an inflammatory bowel disease, especially Crohn's disease, comprising orally administering to the patient an effective amount of a pharmaceutical composition in dosage unit form comprising a spherical activated carbon having a particle size of 0.05 to 2 mm, a specific surface area of 500 to 2,000 $m^2/g$ and a specific pore volume of 0.2 to 2.0 ml/g determined in the range of a pore radius of not more than 80 Å.

In a fourth aspect of the invention, there is provided a method of treating a patient suffering from a complication of inflammatory bowel diseases with hemorrhoids diseases and/or stoma-peripheral inflammation diseases, comprising orally administering to the patient an effective amount of a pharmaceutical composition in dosage unit form comprising a spherical activated carbon having a particle size of 0.05 to 2 mm.

In a fifth aspect of the invention, there is provided a method of treating a patient suffering from a complication of inflammatory bowel diseases with hemorrhoids diseases and/or stoma-peripheral inflammation diseases, comprising orally administering to the patient an effective amount of a pharmaceutical composition in dosage unit form comprising a spherical activated carbon having a particle size of 0.05 to 2 mm and produced by heat-treating a porous and spherical carbonaceous substance obtainable from a petroleum-based heavy hydrocarbon (petroleum pitch) in an oxidative atmosphere and further heat-treating the thus obtained substance in an atmosphere inert to carbon.

In a sixth aspect of the invention, there is provided a method of treating a patient suffering from a complication of inflammatory bowel diseases with hemorrhoids diseases and/or stoma-peripheral inflammation diseases, comprising orally administering to the patient an effective amount of a pharmaceutical composition in dosage unit form comprising a spherical activated carbon having a particle size of 0.05 to 2 mm, a specific surface area of 500 to 2,000 $m^2/g$ and a specific pore volume of 0.2 to 2.0 ml/g determined in the range of a pore radius of not more than 80 Å.

DETAILED DESCRIPTION OF THE INVENTION

The activated carbon used as an active ingredient of the therapeutic agent for inflammatory bowel diseases according to the present invention is a spherical activated carbon having a particle size of 0.05 to 2 mm, preferably 0.1 to 1.0 mm, which is usable internally for medicinal application. When the particle size of the spherical activated carbon is less than 0.05 mm, harmful side effects such as constipation, etc. may be caused on administration of such spherical activated carbon, and when its particle size exceeds 2 mm, such spherical activated carbon is not only hard to be taken by patient but also slow to take effect.

It is preferable that the spherical activated carbon used in the present invention has high adsorptivity. For this purpose, the spherical iactivated carbon is preferably one which has a specific surface area of 500 to 2,000 $m^2/g$. The specific surface area has been determined according to the methanol adsorption method using an automatic adsorption meter.

For producing the spherical activated carbon used in the present invention, there can be used suitable raw materials which are easily available, such as sawdust, coal, coconut shell flour, petroleum or coal pitches, or organo-synthetic high polymeric substances. The spherical activated carbon is produced by a process of carbonizing the raw material and activating the obtained carbon. Various processes for activation such as a steam activation process, chemicals activation process, an air activation process, a carbon dioxide activation, etc., can be used.

Examples of the spherical activated carbons available for use in the present invention are a granulated spherical activated carbon produced from carbonaceous powders, a spherical activated carbon produced by calcining a resin, and a spherical activated carbon obtainable from petroleum-based heavy hydrocarbons (petroleum pitches). The spherical activated carbon has the advantages over the powdery activated carbon in that the spherical activated carbon does not scatter when administered and also won't cause constipation even if administered continuously, and thus is suited as an active ingredient of the pharmaceutical composition according to the present invention.

Among the spherical activated carbons, those obtainable from petroleum-based heavy hydrocarbons (petroleum pitches), which are homogeneous spherical particles, are preferred.

The granulated activated carbon produced from carbonaceous powders can be obtained by granulating the carbonaceous powder material into microspherical particles with a binder such as tar or pitch, heat-treating the obtained particles at 600° to 1,000° C. in an inert atmospheres for carbonization, and activating the produced carbon particles. Various processes can be used for activation of the carbon particles, such as the steam activation process, the chemicals activation process, the air activation process and the carbon dioxide activation process. The steam activation process, for instance, is carried out at 800° to 1,100° C. in a steam atmosphere.

The spherical activated carbon produced by calcining a resin is produced, for instance, in the manner described in Japanese Patent Application Publication (KOKOKU) No. 61- 1366. For example, a condensation or polyaddition-type thermosetting prepolymer is mixed with a curing agent, curing catalyst, emulsifier, etc., and the obtained mixture is emulsified in water with stirring and reacted while continuing stirring at room temperature or under heating. The reaction system first assumes a state of a suspension, and on further stirring, produces a spherical product of thermosetting resin. This product is recovered and heated at a temperature of not less than 500° C. in an inert atmosphere to carbonize the spherical product, and the obtained spherical carbon product is activated by the method mentioned above.

The spherical activated carbon obtainable from petroleum pitches can be produced, for instance, by the processes such as described below.

In a first process, as for instance described in Japanese Patent Publication (KOKOKU) No. 51-76 (corresponding to U.S. Pat. No. 3,917,806) and Japanese Patent Application Laid Open (KOKAI) No. 54-89010 (corresponding to U.S. Pat. No. 4,761,284), a petroleum pitch having a flow point of 50° to 300° C. is made into spherical particles in a molten state, then infusibilized with oxygen, carbonized at a temperature of 600° to 1,000° C. in an inert atmosphere and activated at a temperature of 850° to 1,000° C. in a steam atmosphere. Carbonization and activation can be accomplished simultaneously by selecting a proper atmosphere.

According to a second method, as for instance described in Japanese Patent Publication (KOKOKU) No. 59-10930 (corresponding to U.S. Pat. No. 4,420,443), a petroleum pitch having a flow point of not less than 160° C. is made into strings, crushed, put into hot water to form spherical particles, infusibilized with oxygen, and then carbonized and activated in the same way as the first process described above.

The spherical activated carbon particles obtained according to the above-described first or second process have a particle diameter of 0.05 to 2.0 mm, preferably 0.1 to 1.0 mm; a specific surface area of 500 to 2,000 $m^2/g$, preferably 1,000 to 2,000 $m^2/g$.

Further, as the activated carbon as an active ingredient of the pharmaceutical composition according to the present invention, a spherical activated carbon obtainable by subjecting to an oxidation and reduction treatments may be usable.

The spherical activated carbon material as a raw material for subjecting to the oxidation and reduction treatments may be either of a porous and spherical carbonaceous substance obtainable from petroleum pitch, a granulated carbon obtainable from carbonaceous powders or a spherical carbon obtainable by calcining a resin, but the porous and spherical carbonaceous substance obtainable from petroleum pitches is preferred.

As the process of the oxidation and reduction treatments at high temperature, a process described in Japanese Patent Publication (KOKOKU) No. 62-11611 (corresponding to U.S. Pat. No. 4,681,764) may be exemplified.

The oxidation treatment at a high temperature is a heat-treatment carried out in an oxidative atmosphere containing oxygen at a high temperature, for example, 300° to 700° C. As the oxygen source, there may be used pure oxygen, nitrogen oxide and air. The reduction treatment at a high temperature is a heat-treatment carried out at a high temperature, for example, 700° to 1,100° C. in an atmosphere inert to carbon. The atmosphere inert to carbon can be formed by using nitrogen gas, argon gas, helium gas or a mixture thereof.

The oxidation treatment is preferably carried out in an atmosphere with an oxygen content of 0.5 to 25% by volume, more preferably 3 to 10% by volume at a temperature of 300° to 700° C., more preferably 400° to 600° C. The reduction treatment is preferably carried out in an inert atmosphere at a temperature of 700° to 1,100° C., more preferably 800° to 1,000° C.

In the production of the spherical activated carbon obtainable from the porous and spherical carbonaceous substance obtainable from petroleum pitches, it is preferred that the oxidation treatment is carried out at a temperature of 350° to 700° C. in an oxidative atmosphere and then the heat-treatment is carried out at a temperature of 800° to 1,000° C. in an atmosphere inert to carbon.

More in detail, the process for producing the spherical activated carbon obtainable from the porous and spherical carbonaceous substance obtainable from petroleum pitches, which comprises the steps of:

(1) blending a petroleum-based heavy hydrocarbon (petroleum pitch) of a H/C ratio of 0.45 to 0.80 and a flow point of 100° to 300° C., in which the presence of unevenly distributed anisotropic regions is not observed under a polarization microscope, with an aromatic hydrocarbon such as benzene and naphthalene;

(2) dispersing the obtained mixture in hot water at 100° to 180° C. containing a surfactant while stirring the resultant dispersion, to form particles thereof;

(3) after cooling the resultant dispersion to room temperature, separating the thus formed particles by filtration;

(4) removing the aromatic hydrocarbon contained in the particles by extraction with an organic solvent such as hexane and methanol;

(5) contacting the thus extract-treated particles with a flow of oxidative gas to carry out the oxidation of the particles (infusibilization);

(6) heating the thus infusibilized particles in a flow of a gas which is reactive with carbon, such as steam and carbon dioxide, at a temperature of 800° to 1,000° C. (carbonization and activation);

(7) heat-treating the thus obtained porous and spherical carbonaceous substance at a temperature of 350° to 700° C. in an atmosphere containing 0.5 to 20% by volume of oxygen; and (8) further heat-treating the thus obtained substance at a temperature of 800° to 1,000° C. in an atmosphere inert to carbon.

Such spherical activated carbon subjected to the oxidation and reduction treatments have a particle diameter of 0.05 to 2.0 mm, preferably 0.1 to 1.0 mm; a specific surface area of 500 to 2,000 $m^2/g$, preferably 1,000 to 2,000 $m^2/g$; and a specific pore volume of 0.2 to 2.0 ml/g determined in the range of pore-radius of less than 80 Å.

As an example of the spherical activated carbon obtained by subjecting the porous and spherical carbonaceous substance derived from the petroleum pitches to the oxidation and reduction treatments, KREMEZIN (produced by Kureha Chemical Industries Co., Ltd.) used as an oral therapeutic agent for a chronic renal failure, can be cited.

KREMEZIN is a spherical activated carbon produced by the process disclosed in Japanese Patent Publication (KOKOKU) No. 62-11611 (corresponding to U.S. Pat. No. 4,681,764), which has a particle size of about 0.2 to 0.4 mm and is a homogeneous spherical particle (which is not spherical particle produced by granulating a carbon powder).

When KREMEZIN which is a commercially available spherical activated carbon used as an oral therapeutic agent for a chronic renal failure and one of the spherical activated carbons usable in the present invention, is orally administered to the patients suffering from Crohn's disease, there is observed quite surprisingly a definite therapeutic effect of the spherical activated carbon, leading to a remarkable betterment of the disease. Further, no side effect such as constipation is caused after administration of the spherical activated carbon. In view of these facts, it is recognized that the pharmaceutical composition of the present invention comprising the spherical activated carbon as an active ingredient is useful as a therapeutic agent for inflammatory bowel diseases such as Crohn's disease and ulcerative colitis, especially for the treatment of Crohn's disease.

Further, when KREMEZIN is orally administered to the patients suffering from Crohn's disease complicated with perianal fistula diseases and the patients suffering from Crohn's disease complicated with stoma (enteroproctia)-peripheral inflammation diseases, there is noted quite surprisingly a remarkable improvement of the diseases, indicating a definite therapeutic effect of the spherical activated carbon for Crohn's disease complicated with perianal fistula diseases and Crohn's disease complicated with stoma (enteroproctia)-peripheral inflammation diseases.

From the result of an acute toxicity test, it is determined that $LD_{50}$ of the spherical activated carbon according to the present invention is not less than 5,000 mg/kg. Also, in an anatomical examination conducted two weeks after and in the observation of external appearance and the viscera, there is seen no noteworthy abnormality nor any notable toxic symptoms. Further, in a subacute toxicity test, there is observed no notable abnormality nor toxic symptoms attributable to administration of the specimen. These facts attest to very high safety of the spherical activated carbon according to the present invention.

The pharmaceutical composition for inflammatory bowel diseases according to the present invention can be applied to man and mammals. It is preferably administered orally. The dosage of the pharmaceutical composition depends on the subject of administration (man or animal), age thereof, individual difference, condition of the disease and other factors. For human, the dosage of the pharmaceutical composition (calculated as the amount of the spherical activated carbon) is usually 0.2 to 20 g, preferably 1 to 10 g per day. The dosage may be properly increased or decreased according to the condition of the disease. Also, a day's dose of the pharmaceutical composition according to the present invention may be administered all at once or in portions.

Spherical activated carbon may be administered in the form as it is or in the form of a pharmaceutical preparation. In the former case, activated carbon may be suspended in drinking water to form a slurry which is convenient to take.

The pharmaceutical preparations comprising activated carbon may take a diversity of forms such as granule, tablet, sugar-coated tablet, capsule, stick, divided package, suspension, etc. In the case of capsule, it may not necessarily be ordinarily used gelatin capsule, enteric-diffluent capsule may be used as occasion demand. In case the composition is used in the form of granules, tablet or sugar-coated tablet, such granules or tablets need to be released into the original form of spherical activated carbon particles in the viscera. The content of spherical activated carbon in the pharmaceutical compositions is usually 1 to 100 wt. %. In the present invention, the preferred forms of pharmaceutical preparation comprising spherical activated carbon are capsule, stick and divided package. In these preparations, spherical activated carbon is encapsulated or packed in a container in the form as it is.

Capsules can be obtained by, for example, encapsulating 200 mg of spherical activated carbon in a gelatin capsule.

Sticks can be prepared by, for example, packing 2 g of spherical activated carbon in a stick composed of a laminate film and heat-sealing the packed stick.

The pharmaceutical composition of the present invention, which is administered orally, shows a definite therapeutic effect for the inflammatory bowel diseases such as Crohn's disease and ulcerative colitis diseases, especially Crohn's disease.

The pharmaceutical composition of the present invention, which is administered orally, shows a definite therapeutic effect for complication of inflammatory bowel diseases such as Crohn's disease and ulcerative colitis diseases with perianal fistula diseases, stoma (enteroproctia)-peripheral inflammation diseases or perianal fistula diseases and stoma (enteroproctia)-peripheral inflammation diseases.

EXAMPLES

The present invention is explained in more detail in the following Examples, however, it should be recognized that the scope of the invention is not restricted to these Examples.

Production Example

Preparation of spherical activated carbon

Three hundred grams of a petroleum-based heavy hydrocarbon (petroleum pitch) having an H/C ratio of 0.55 and a flow point of 220° C. and not having localized presence of an isotropic region in observation under a polarization microscope, and 100 g of naphthalene were introduced into an autoclave provided with a stirrer, and the obtained mixture was further mixed well at a temperature of 180° C. Into the thus obtained liquid mixture was added 1,200 g of an aqueous 0.5% solution of polyvinyl alcohol. Then the resultant mixture was vigorously stirred at a temperature of 140° C. for 30 minutes and cooled to room temperature with stirring to form a dispersion of spherical particles. After separating the spherical particles therefrom, the obtained spherical particles were treated with hexane in an extractor to remove naphthalene contained in the particles and dried by air flow. The thus obtained spherical particles were heated to 300° C. at a rate of 25° C./hr by a flow of heated air in a fluidized bed and further kept for 2 hours at the same temperature. The obtained spherical particles were heated to 900° C. by steam in a fluidized bed and further kept for 2 hours at the same temperature to obtain spherical carbonaceous particles.

The obtained spherical carbonaceous particles were heated to 610° C. in an atmosphere containing 3% by volume of oxygen and further kept at the same temperature for 3 hours in the same atmosphere. Then the treated spherical carbonaceous particles were further heated to 940° C. in an atmosphere of nitrogen and then kept at the same temperature for 30 minutes in the same atmosphere to obtain spherical activated carbon (spherical particulate activated carbon having a particle size of about 0.2 to about 0.4 mm, obtained by subjecting spherical and porous particulate carbonaceous substance produced from a petroleum-based heavy hydrocarbon (petroleum pitch) to the oxidation and reduction treatments at a high temperature).

The obtained spherical activated carbon was homogeneous and substantially truly spherical particles, and had a particle diameter of about 0.2 to about 0.4 mm, a specific surface area of 1520 $m^2/g$, and a specific pore volume of 0.72 ml/g determined in the range of a pore-radius of not more than 80 Å.

Test Example

Toxicity test on spherical activated carbon obtained in the production example

In an acute toxicity test of the spherical activated carbon by oral administration to the rats (Cpb:WU; Wister-Random), no abnormality was observed even at the maximum dosage (5,000 mg/kg for male and female rats) according to the Guidelines for Toxicity Studies of Drugs (Notification No. 118 of the Pharmaceutical Affairs Bureau, Ministry of Health and Welfare, Japanese Government, Feb. 15, 1984).

Example 1

Effect on enteral (small intestinal) Crohn's disease

The subject was a man (26 years old) who had developed the symptoms of small intestinal Crohn's disease 5 years ago and had a home elemental enteral nutrition (HEEN) treatment with little improvement of the disease. Then he had an intravenous hyperalimentation (IVH) treatment for a period of one year and 4 months, and was hospitalized three times during this period. However, he had repeated relapse of the disease and was rehospitalized, with the IVH treatment restarted immediately after hospitalization. No improvement of the disease was seen even after the lapse of 2 months from start of the IVH treatment. Also, administration of antibiotics produced no therapeutic effect.

When the capsules containing 200 mg of the spherical activated carbon obtained in the above Production Example was administered to the patient at a ratio of 30 capsules per day, there were noted the signs of improvement of the condition of the disease, such as drastic decrease of secretion of pus, with no constipation caused, at the 4th day after start of administration of the spherical activated carbon. The leukocyte count (WBC) of the patient also has dropped from $11,200/mm^3$ to $6,800/mm^3$. One month after start of administration, the treatment was switched to HEEN, and the capsules of the spherical activated carbon have been administered to the patient at the ratio for a period of about 3 months. As a result, the patient suffered no relapse of the disease and was allowed to leave the hospital as he has made satisfactory progress.

Example 2

Effect on enteric Crohn's disease complicated with rectal fistula and vaginal fistula diseases The subject was a woman (32 years old) suffering from enteric Crohn's disease for the past 15 years, which was complicated with rectal fistula and vaginal fistula diseases two years ago. Home IVH was conducted on this patient but no improvement of the disease was made after one-month treatment.

When the capsules containing 200 mg of the spherical activated carbon obtained in the Production Example were administered to the patient at a ratio of 30 capsules per day, there were noted the signs of improvement of the condition of the disease, such as sharp decrease of secretion of pus, with no constipation caused, at the 4th day after start of administration of the spherical activated carbon, and in about 6 weeks after start of administration, redness and swelling of the vagina and its limbic region, secretion of pus from the vagina and anal region, and pain at the anal to genital region have disappeared, and the patient became able to sit down on her legs. Hitherto, there has been no positive remedy for the above troubles except for nutrition treatment to increase the patient's physical strength, but administration of the spherical activated carbon according to the present invention has produced a remarkable therapeutic effect for the enteric Crohn's disease complicated with rectal fistula and vaginal fistula diseases.

Example 3

Effect on Crohn's disease complicated with cutaneous erosion around ileac stoma

The subject was a man (26 years old) suffering from Crohn's disease. He had undergone an ileostomy because of stricture at the termination of the ileum and partial abdominal abscess four years ago. Redness and ulceration of the skin around the ileac stoma occurred frequently. Various treatments were applied for eliminating these troubles, but in vain. When the capsules containing 200 mg of the spherical activated carbon obtained in the Production Example were administered to the patient at a ratio of 30 capsules per day, there were noted the signs of improvement of the condition of the disease, such as sharp decrease of secretion of pus, at the 4th day after start of administration of the spherical activated carbon. Also, the cutaneous lesion around the ileac stoma took a turn for the better, and it perfectly disappeared on the 7th day after start of administration. Thus, administration of the spherical activated carbon of the present invention has produced a remarkable therapeutic effect for the enteric disease complicated with cutaneous ulceration around the ileac stoma.

Example 4

Effect on enteric Crohn's disease complicated with Fistulae in the Intestinal Tract and Anal Region)

The subject was a man (22 years old) suffering from an enteric Crohn's disease complicated with the fistulae in the intestinal tract and anal region with frequent occurrence of diarrhea and stomachache for a long time. The dietetic and steroidal medicinal treatments produced no appreciable therapeutic effect. The patient has suffered from inveterate diarrhea and had a weight loss.

When the capsules containing 200 mg of the spherical activated carbon obtained in the Production Example were administered to the patient at a ratio of 21 capsules per day, there was noted the improvement of the pathemas such as diarrhea and stomachache caused by the Crohn's disease, with no constipation caused, on the 4th day after start of administration thereof, and the disease took a favorable turn in two weeks after start of administration. Further, when the dosage of the spherical activated carbon capsules was increased to 30 capsules per day, the symptoms of both intestinal and anal fistulae have improved, and the fistulae have cured in four weeks after start of administration of the increased dose of the spherical activated carbon. Hitherto, there have been available no effective treatment for the Crohn's disease complicated with fistula such as mentioned above, but a remarkable curative effect for the enteric Crohn's disease complicated with the intestinal and anal fistulae has been produced by the oral administration of the spherical activated carbon of the present invention.

Example 5

Effect on Crohn's disease complicated with cutaneous ulceration around stoma

The subject was a man (28 years old) suffering from an enteric Crohn's disease. The patient has had a continuous nutrition treatment, but since he had intestinal stenosis of sigmoid colon and anal fistula, he has undergone colosigmoidostomy. Then the underlying Crohn's disease recurred and the patient complained of nausea, stomachache and fervescence, and suffered from frequent occurrence of redness, ulceration and swelling of the skin around the stoma. He also showed resistance to medication with steroids, etc., and was hospitalized. When the capsules containing 200 mg of the spherical activated carbon obtained in the Production Example were administered to the patient at a ratio of 30 capsules per day, the inflammation such as erosion around the stoma was improved in 3 to 4 days after start of administration. The subjective and objective symptoms of the Crohn's disease, such as recrudescent nausea, vomiting, stomachache and fervescence, were also alleviated in two weeks of dosing of the spherical activated carbon, and the patient was allowed to leave the hospital. Thus, dosing of the spherical activated carbon of the present invention produced a remarkable therapeutic effect for the enteric Crohn's disease complicated with cutaneous erosion around stoma.

What is claimed is:

1. A method of treating a patient suffering from ulcerative colitis or Crohn's disease, comprising orally administering to said patient symptom-alleviating amount of a pharmaceutical composition in dosage unit form comprising a spherical activated carbon having a particle size of 0.05 to 2 mm.

2. A method according to claim 1, wherein said spherical activated carbon is produced by heat-treating a porous and spherical carbonaceous substance obtained form a petroleum-based heavy hydrocarbon in an oxidative atmosphere and further heat-treating the obtained substance in an atmosphere inert to carbon.

3. A method of treating a patient suffering from complications of ulcerative colitis or Crohn's disease with hemorrhoids, stoma-peripheral inflammation, or both hemorrhoids and stoma-peripheral inflammation, comprising orally administering to said patient a symptom alleviating effective amount of a pharmaceutical composition in dosage unit form comprising a spherical activated carbon having a particle size of 0.05 to 2 mm.

4. A method according to claim 3, wherein said spherical activated carbon is produced by heat-treating a porous and spherical carbonaceous substance obtained from a petroleum-based heavy hydrocarbon in an oxidative atmosphere and further heat-treating the obtained substance in an atmosphere inert to carbon.

5. A method according to claim 1, wherein the amount of the pharmaceutical composition administered in dosage unit form is 0.2 to 20 g, calculated as the spherical activated carbon, per day.

6. A method according to claim 3, wherein the amount of the pharmaceutical composition administered in dosage unit form is 0.2 to 20 g, calculated as the spherical activated carbon, per day.

7. A method of treating a patient suffering from ulcerative colitis or Crohn's disease, comprising orally administering to said patient symptom alleviating amount of a pharmaceutical composition in dosage unit form comprising a spherical activated carbon having a particle size of 0.05 to 2 mm, said spherical activated carbon produced by heat-treating a porous and spherical carbonaceous substance obtained from a petroleum-based heavy hydrocarbon in an oxidative atmosphere and further heat-treating the thus obtained substance in an atmosphere inert to carbon.

8. A method of treating a patient suffering from complications of ulcerative colitis or Crohn's disease with hemorrhoidal disease, stoma-peripheral inflammation disease, or hemorrhoidal disease and stoma-peripheral inflammation disease, comprising orally administering to said patient a symptom alleviating amount of a pharmaceutical composition in dosage unit form comprising a spherical activated carbon having a particle size of 0.05 to 2 mm, said spherical activated carbon produced by heat-treating a porous and spherical carbonaceous substance obtained from a petroleum-based heavy hydrocarbon in an oxidative atmosphere and further heat-treating the obtained substance in an atmosphere inert to carbon.

9. The method according to claim 1, wherein the disease is Crohn's disease.

10. The method according to claim 3, wherein the disease is Crohn's disease.

11. The method according to claim 7, wherein the disease is Crohn's disease.

12. The method according to claim 8, wherein the disease is Crohn's disease.

* * * * *